United States Patent [19]
Brindell et al.

[11] 3,941,850

[45] Mar. 2, 1976

[54] α, α, α', α'-TETRAKIS(4-HYDROXY-3,5-DISBUSTITUTED PHENYL)XYLENE

[75] Inventors: Gordon D. Brindell, Crystal Lake; Joseph P. Wuskell, Barrington, both of Ill.

[73] Assignee: The Quaker Oats Company, Chicago, Ill.

[22] Filed: Mar. 15, 1974

[21] Appl. No.: 451,456

Related U.S. Application Data

[62] Division of Ser. No. 252,859, May 12, 1972, Pat. No. 3,836,590.

[52] U.S. Cl. ... 260/619 A; 260/45.95 R; 260/619 B
[51] Int. Cl.² ................ C07C 39/12; C07C 39/16
[58] Field of Search .................. 260/619 B, 619 A

[56] References Cited

UNITED STATES PATENTS

| | | | |
|---|---|---|---|
| 3,026,297 | 3/1962 | Spacht | 260/619 B |
| 3,309,337 | 3/1967 | Hurlock et al. | 260/619 B |
| 3,350,347 | 10/1967 | Casey | 260/45.95 |
| 3,393,244 | 7/1968 | Broderick | 260/619 B |
| 3,642,669 | 2/1972 | Mast et al. | 260/45.95 |
| 3,689,572 | 9/1972 | Ruppert | 260/619 B |

*Primary Examiner*—Norman Morgenstern
*Attorney, Agent, or Firm*—Joseph P. O'Halloran

[57] ABSTRACT

A new series of compounds defined broadly as α,α,α',α'-tetrakis(4-hydroxy-3,5-disubstituted phenyl)-xylenes, which are useful as antioxidants for organic materials normally subject to oxidative deterioration, is disclosed.

2 Claims, No Drawings

α,α,α',α'-TETRAKIS(4-HYDROXY-3,5-DISUBSTITUTED PHENYL)XYLENE

This is a division of application Ser. No. 252,859 filed May 12, 1972, now U.S. Pat. No. 3,836,590.

BACKGROUND OF THE INVENTION

1. Field of the Invention

This invention relates to a new class of antioxidants.

2. Description of the Prior Art

Tetra-2,5-disubstituted phenolic derivatives of phthalaldehyde having the following formula are known as antioxidants:

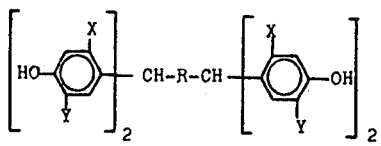

wherein R is o-, m-, or p-phenylene and X and Y are alkyl groups.

We have unexpectedly found that the tetra-2,6-disubstituted phenolic derivatives are superior antioxidants.

SUMMARY OF THE INVENTION

Accordingly, one object of the present invention is to provide a novel tetraphenolic derivative of phthalaldehyde which is useful as an antioxidant.

Another object is to provide an organic material normally tending to undergo oxidative deterioration which has been stabilized with a novel tetraphenolic derivative of phthalaldehyde.

Other objects will be apparent to one skilled in the art in view of the following description of the invention.

The objects of this invention are accomplished by a composition having the formula:

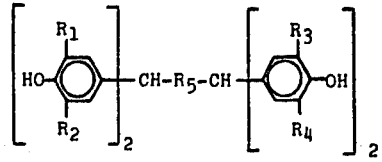

wherein $R_1$, $R_2$, $R_3$, and $R_4$ are independently selected from the group consisting of alkyl and aralkyl and $R_5$ is o-, m-, or p-phenylene.

The objects of this invention are further accomplished by organic material normally tending to undergo oxidative deterioration in the presence of air or oxygen containing an effective amount of a composition having the above formula.

By alkyl in the formula we mean methyl, ethyl, propyl, butyl, pentyl, hexyl, heptyl, etc. and where the alkyl group contains three or more carbon atoms may be straight or branched chain. We prefer that the alkyl group contains from one to ten carbon atoms. Preferred alkyl groups include for example, methyl, ethyl, isopropyl, isobutyl, sec-butyl, tert-butyl, 1-methylbutyl, tert-pentyl, 2-methylbutyl, neopentyl, 1-methylpentyl, 1,1-dimethylpentyl, 1-ethylpentyl, 1,1-diethylpentyl, 2-methylpentyl, 2,2-dimethylpentyl, 2-ethylpentyl, 2,2-diethylpentyl, 1-methylhexyl, 1,1-dimethylhexyl, 1-ethylhexyl, 2-methylhexyl, 2,2-dimethylhexyl, 2-ethylhexyl, etc.

The aralkyl in the formula may be benzyl, styryl chlorobenzyl, bromobenzyl, iodobenzyl, fluorobenzyl, methoxybenzyl, ethoxybenzyl, methylbenzyl, ethylbenzyl, or tert-butylbenzyl for example. We prefer that the aralkyl group contains less than 20 carbon atoms. Where the alkylene portion of the aralkyl group contains two or more carbons, the alkylene group may be straight or branched chain. We prefer that the aralkyl group is substituted with a group which is halo, alkoxy, or alkyl. Any substitution is on the aryl portion of the aralkyl group and may be made for one or all of the available hydrogens. Suitable halo groups include chloro, bromo, iodo, and fluoro. Suitable alkoxy and alkyl groups include those containing from 1 to 13 carbon atoms.

Exemplary tetra-2,6-disubstituted phenolic derivatives of phthalaldehyde include the following: α, α, α', α'-tetrakis(4-hydroxy-3,5-dimethylphenyl)xylene; α, α, α', α'-tetrakis(4-hydroxy-3,5-diethylphenyl)xylene; α, α, α', α'-tetrakis(4-hydroxy-3,5-dipropylphenyl)zylene; α, α, α', α'-tetrakis(4-hydroxy-3,5-dibutylphenyl)xylene; α, α, α', α'-tetrakis(4-hydroxy-3,5-dipentylphenyl)xylene; α, α, α', α'-tetrakis(4-hydroxy-3,5-dihexylphenyl)xylene; α, α, α', α'-tetrakis(4-hydroxy-3,5-diisopropylphenyl)xylene; α, α, α', α'-tetrakis(4-hydroxy-3,5-diisobutylphenyl)xylene; α, α, α', α'-tetrakis(4-hydroxy-3,5-di-sec-butylphenyl)xylene; α, α, α', α'-tetrakis(4-hydroxy-3,5-di-tert-butylphenyl)xylene; α, α, α', α'-tetrakis[4-hydroxy-3,5-di(1-methylbutyl)phenyl]xylene; α, α, α', α'-tetrakis(4-hydroxy-3,5-di-tertpentylphenyl)xylene; α, α, α', α'-tetrakis[4-hydroxy-3,5-di-(2-methylbutyl)phenyl]xylene; α, α, α', α'-tetrakis(4-hydroxy-3,5-dineopentylphenyl)xylene; α, α, α', α'-tetrakis[4-hydroxy-3,5-di(1-methylpentyl)phenyl]xylene; α, α, α', α'-tetrakis[4-hydroxy-3,5-di(1,1-dimethylpentyl)phenyl]xylene; α, α, α', α'-tetrakis[4-hydroxy-3,5-di(1-ethylpentyl)phenyl]xylene; α, α, α', α'-tetrakis[4-hydroxy-3,5-di(1,1-diethylpentyl)phenyl]xylene; α, α, α', α'-tetrakis[4-hydroxy-3,5-di(2-methylpentyl)phenyl]xylene; α, α, α', α'-tetrakis[4-hydroxy-3,5-di(2,2-dimethylpentyl)phenyl]xylene; α, α, α', α'-tetrakis-[4-hydroxy-3,5-di(2-ethylpentyl)phenyl]xylene; α, α, α', α'-tetrakis[4-hydroxy-3,5-di(2,2-diethylpentyl)phenyl]xylene; α, α, α', α'-tetrakis[4-hydroxy-3,5-di(1-methylhexyl)phenyl]xylene; α, α, α', α'-tetrakis[4-hydroxy-3,5-di(1-ethylhexyl)phenyl]xylene; α, α, α', α'-tetrakis[4-hydroxy-3,5-di(1,1-diethylhexyl)phenyl]xylene; α, α, α', α'-tetrakis[4-hydroxy-3,5-di(2-methylhexyl)phenyl]xylene; α, α, α', α'-tetrakis[4-hydroxy-3,5-di(2,2-dimethylhexyl)phenyl]xylene; α, α, α', α'-tetrakis[4-hydroxy-3,5-di(2-ethylhexyl)phenyl]xylene; α, α, α', α'-tetrakis[4-hydroxy-3,5-di(2,2-diethylhexyl)phenyl]xylene; α, α, α', α'-tetrakis(4-hydroxy-3,5-dibenzylphenyl)xylene; α, α, α', α'-tetrakis[4-hydroxy-3,5-di(p-chlorobenzyl)phenyl]xylene; α, α, α', α'-tetrakis[4-hydroxy-3,5-di(p-bromobenzyl)phenyl]xylene; α, α, α', α'-tetrakis[4-hydroxy-3,5-di(p-iodobenzyl)phenyl]xylene; α, α, α', α'-tetrakis[4-hydroxy-3,5-di(p-fluorobenzyl)phenyl]xylene; α, α, α', α'-tetrakis[4-hydroxy-3,5-di(-nonylbenzyl)phenyl]xylene; α, α, α', α'-tetrakis[4-hydroxy-3,5-di(p-methoxybenzyl)phenyl] xylene; α, α, α', α'-tetrakis(4-hydroxy-3-tert-butyl-5-methylphenyl)xylene; α, α, α', α'-tetrakis(4-hydroxy-3,5-distyrylphenyl)xylene; α, α, α', α'-tetrakis[4-hydroxy-3,5-di(p-methylbenzyl)phenyl]xylene; and α, α, α', α'-tetrakis[4-hydroxy-3,5-di(o-chlorobenzyl)phenyl]xylene.

The tetraphenolic derivatives of our invention may be obtained by permitting substantially four moles of a phenol to react with phthalaldehyde in the presence of an acidic catalyst.

The reaction is preferably carried out in an inert solvent, for example an alcohol such as methanol, ethanol, 2-propanol, ethylene glycol, ethylene glycol monoethyl ether, etc. Ethanol is the preferred solvent since it allows solubility of the reactants and, in many cases, crystallization of the product directly from solution. The reaction is most conveniently carried out at the reflux temperature of the solvent for 0.5 to about 24 hours. We prefer the reaction temperature to be about 60° to 65°C. In those cases where the product does not precipitate on cooling, it may be readily isolated by removal of the solvent or by dilution with water. Liquid products may be isolated in this manner.

Suitable phenols for use in preparing the tetraphenolic compounds include those of the formula:

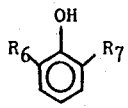

wherein $R_6$ and $R_7$ are consistent with $R_1$, $R_2$, $R_3$, and $R_4$ as defined above. All of the suitable phenols are commercially available or readily prepared by known techniques.

The reaction is preferably carried out in the presence of an acid catalyst. Acidic catalysts include organic acids, inorganic acids, and Friedel-Crafts catalysts. Suitable organic acids for example are the phosphoric and sulfonic acids such as phosphoric acid, pyrophosphoric acid, ethanesulfonic, benzenesulfonic acid, toluenesulfonic acid, and naphthalenesulfonic acid. Suitable inorganic acids include the mineral acids such as sulfuric acid and hydrochloric acid. Friedel-Crafts catalysts including aluminum chloride, boron trifluoride, ferric chloride, zinc chloride, and the like, may also be employed.

The catalysts are employed in a catalytic amount which depends on the reactants and reaction conditions. For example, the amount may range from about 2 to 500 parts of catalyst per 100 parts by weight of the phenol. Preferred concentrations of the catalyst are about 80 to about 150 parts on the same basis.

The tetraphenolic compounds of our invention are useful as antioxidants for organic materials normally tending to undergo oxidative deterioration. By organic material normally tending to undergo oxidative deterioration, we mean to include material based in whole or in part on a skeleton comprising interconnected carbon atoms which upon exposure to oxygen or air loses its desirable properties and becomes weak, brittle, cracked, discolored, viscous or the like. Exemplary organic materials are polymers; hydrocarbon liquids, particularly gasoline and lubricating or fuel oils, hydrocarbon solids or semi-solids, such as waxes, greases and the like; elastomers, such as natural and synthetic rubber and feeds or foodstuffs.

Typical polymers include polyolefins, polyurethanes, polyethers, and polyamides. Suitable polyolefins include for example polystyrene, polyvinyl chloride, polyvinylidene chloride, polyvinyl fluoride, polyvinyl butyral, polymethyl acrylate, ethylene vinyl acetate copolymers, and ethylene propylene terpolymers. Suitable polyethers include for example polyformaldehyde and polytetramethylene ether glycol.

Hydrocarbon liquids stabilized by our novel tetraphenolic derivatives include motor lubricating oils, gear and transmission fluids based on hydrocarbon oils, and the like. Fuel oils, such as furnace oils and light kerosene fractions, including gas turbine fuels, are also stabilized by our compositions.

Solid or semi-solid hydrocarbons, such as wax and grease, are also improved by incorporation therein of the tetraphenolic compounds of this invention.

Such solid polymeric elastomers as natural and synthetic rubber are stabilized against hardening, cracking, and checking with the tetraphenolic derivatives described. Exemplary of natural rubbers is *Hevea brasiliensis*, while synthetic rubbers include styrene-butadiene rubber; polybutadiene; polyisoprene; neoprene, butyl rubber; nitrile-butadiene rubbers, styrene-chloroprene rubbers; acrylate-butadiene rubbers; and polyurethane rubber.

The tetraphenolic derivatives of this invention are also useful to enhance the stability of the natural fats and oils. For example, the following edible oils can be stabilized with our compositions: shortening, lard, butter, coconut oil, cotton seed oil, soybean oil, palm oil, corn oil, peanut oil, sunflower seed oil, safflower oil, olive oil, and the like or mixtures thereof. These oils may have been treated, as by hydrogenation, interesterification, or fractional crystallization, to modify their melting points.

In general the tetraphenolic derivatives of our invention should be used with the organic material to be stabilized in an amount effective and sufficient to stabilize the material. The requisite amount will, of course, depend both on the efficiency of the particular tetraphenolic derivative and on the nature of the normally oxidizable substrate in which it is employed. It has been our experience that from 0.01 to 10 percent by weight based on the weight of the organic material is sufficient. Amounts down to as little as 0.0001 percent by weight may be effective in some cases.

It is to be understood that the stabilizing effect of the tetraphenolic compounds is considerably enhanced by conventional synergists such as certain sulfides and poly sulfides. The synergist is used in conventional amounts. For example, an amount of synergist from about 0.1 to about 1 percent by weight of the organic material to be stabilized is satisfactory but we prefer to use from 0.1 to 0.5 percent by weight.

As sulfides there may be mentioned dialkylsulfides, particularly wherein the alkyl groups are long chain such as dodecyl groups since the lower dialkylsulfides are too volatile to be effective, di(substituted)alkylsulfides particularly esters of bis-carboxyalkyl sulfides such as dilauryl, distearyl, ditridecyl, or dioctadecyl thiodipropionates or thiodibutyrates, dibenzylsulfide such as bis(2hydroxy-5-methylbenzyl)sulfide and bis(3-tert-butyl-2-hydroxy-5-methoxybenzyl) sulfide, diaryl sulfide, sulfides such as diphenyl sulfide, dicresyl sulfide, 2:2'-dihydroxy5:5'-dimethyl diphenyl, diphenyldisulfide, dialkyldithiophosphates such as bis(-diisopropyldithiophosphoryl)disulfide, and dialkyldithiophosphatomethylphenols.

It will further be understood that the organic material in addition to containing a stabilizing amount of tetraphenolic compound and a synergist may contain such other ingredients as other antioxidants, coloring agents, fillers, curing agents, etc.

TABLE I

| Test No. | Phenol | Product Tetraphenolic Derivative | M.P. (°C.) | Composition (Percent by Weight) | | | |
|---|---|---|---|---|---|---|---|
| | | | | Calculated | | Found | |
| | | | | C | H | C | H |
| 1 | 2,6-dimethyl-phenol | α,α,α',α'-tetrakis(4-hydroxy-3,5-dimethylphenyl) p-xylene | 254–259 | 81.9 | 7.2 | 81.8 | 7.4 |
| 2 | 2,6-diisobutyl-phenol | α,α,α',α'-tetrakis(4-hydroxy-3,5-diisobutylphenyl) p-xylene | 149–151 | 83.2 | 9.8 | 83.5 | 9.9 |

DESCRIPTION OF THE PREFERRED EMBODIMENTS

The following embodiments of this invention are shown for the purpose of illustrating the invention and demonstrating the best mode for practicing the invention. It will be apparent to those skilled in the art that various changes and modifications may be made therein without departing from the spirit and scope of the invention as it is more precisely defined in the subjoined claims.

EXAMPLE 1

In a 500 ml 3-neck flask equipped with a stirrer, condenser, nitrogen inlet, and a thermometer, 50 ml of methanol and 20 ml of concentrated sulfuric acid were admixed and cooled to 15°C. Then 6.7 g of terephthalaldehyde, 42 g of 2,6-di-tert-butyl phenol, and 50 ml of methanol were combined in a beaker and immediately added to the stirred mixture in the flask. The reaction mixture was then held at 65°C. under a nitrogen atmosphere for 5 hours. The reaction mixture was then cooled to room temperature (27°C.) and allowed to stand overnight. The product was separated from the reaction mixture by filtration, was triturated with ethanol, washed with water until the water washes were neutral, and dried in an oven at 50°C.

The product was identified as α, α, α', α'-tetrakis(4-hydroxy-3,5-di-tert-butylphenyl) p-xylene. Analysis of the product afforded the following data: M.P. between 272° and 281°C., and analyzing to C, 83.1 percent; H, 10.0 percent. $C_{64}H_{90}O_4$ requires C, 83.2 percent; H, 9.8 percent.

EXAMPLE 2

Using the method of Example 1, the following tetraphenolic derivatives were readily prepared in excellent yields from the phenols noted and were found to have the properties reported in Table I.

EXAMPLE 3

Again using the method of Example 1, the following tetraphenolic derivatives were prepared in excellent yields from the phenols noted and were found to have the melting points reported in Table II

TABLE II

| Test No. | Phenol | Product Tetraphenolic Derivative | M.P. (°C.) |
|---|---|---|---|
| 3 | 2-tert-butyl-6-methyl-phenol | α,α,α',α'-tetrakis(4-hydroxy-3-tert-butyl-5-methylphenyl)p-xylene | 219–221 |
| 4 | 2,6-diisopropyl-phenol | α,α,α',α'-tetrakis(4-hydroxy-3,5-diisopropylphenyl)p-xylene | 172–177 |
| 5 | 2,6-di-sec-butyl-phenol | α,α,α',α'-tetrakis(4-hydroxy-3,5-di-sec-butylphenyl)p-xylene | 159–162 |
| 6 | 2,6-di-2-ethyl-hexylphenol | α,α,α',α'-tetrakis[4-hydroxy-3,5-di(2-ethylhexyl)phenyl]p-xylene | Oil at 27°C. |
| 7 | 2,6-dibenzyl-phenol | α,α,α',α'-tetrakis(4-hydroxy-3,5-dibenzylphenyl)p-xylene | 179–184 |
| 8 | 2,6-di-4-methyl-benzylphenol | α,α,α',α'-tetrakis(4-hydroxy-3,5-di-4-methylbenzylphenyl)p-xylene | 183–188 |
| 9 | 2,5-dimethyl-phenol | α,α,α',α'-tetrakis(4-hydroxy-3,6-dimethylphenyl)p-xylene | 324–330 |
| 10 | 2-tert-butyl-5-methylphenol | α,α,α',α'-tetrakis(4-hydroxy-3-tert-butyl-6-methylphenyl)p-xylene | 308–316 |

EXAMPLE 4

A number of candidate antioxidants were evaluated in cis-polyisoprene. The results of these tests are set forth in Table III. Cis-polyisoprene was cut up into small pieces and dissolved overnight in a rapidly stirred solution of 500 ml of toluene. If the antioxidant was readily soluble in toluene, 0.100 g was then added to the cis-polyisoprenetoluene solution and stirred until it dissolved. If the antioxidant was not readily soluble in toluene it was dissolved in a small amount of an appropriate solvent and then added to the toluene solution. A sample of the solution was then taken up in a capillary dropper and 15 drops were placed on a circular sodium chloride plate, 1 inch in diameter. The plate was then put in a 130°C. oven for a few minutes to evaporate the toluene.

An infrared spectrum was run of the film on the plate. The plate was then put back in the oven. Every hour it was removed and another infrared spectrum was run. This procedure was repeated until appreciable oxidation had taken place as indicated by the appearance of a carbonyl band at 1700–1750 $cm^{-1}$. The test was ended when the carbonyl band exceded 6 cm on a Perkin Elmer Infrared Spectophotometer, Model 710. This length is approximately equal to the length of the peak at 1450 $cm^{-1}$.

TABLE III

| Test No. | | Maximum Protection (hours) |
|---|---|---|
| 11 | Blank | 0.5 |
| 12 | α,α,α',α'-tetrakis(4-hydroxy-3,5-dimethylphenyl)p-xylene | 8 |
| 13 | α,α,α',α'-tetrakis(4-hydroxy-3,6-dimethylphenyl)p-xylene | 3 |
| 14 | α,α,α',α'-tetrakis(4-hydroxy-3-tert-butyl-5-methylphenyl)p-xylene | 13 |
| 15 | α,α,α',α'-tetrakis(4-hydroxy-3-tert-butyl-6-methylphenyl)p-xylene | 6 |
| 16 | α,α,α',α'-tetrakis(4-hydroxy-3,5-diisopropylphenyl)p-xylene | 7 |
| 17 | α,α,α',α'-tetrakis(4-hydroxy-3,5-di-sec-butylphenyl)p-xylene | 7 |
| 18 | α,α,α',α'-tetrakis(4-hydroxy-3,5-diisobutylphenyl)p-xylene | 6 |
| 19 | α,α,α',α'-tetrakis(4-hydroxy-3,5-di-tert-butylphenyl)p-xylene | 16 |
| 20 | α,α,α',α'-tetrakis(4-hydroxy-3,5-di-2-ethylhexylphenyl)p-xylene | 3 |
| 21 | α,α,α',α'-tetrakis(4-hydroxy-3,5-dibenzylphenyl)p-xylene | 7 |
| 22 | α,α,α',α'-tetrakis(4-hydroxy-3,5-di-4-methylbenzylphenyl)p-xylene | 6 |

EXAMPLE 5

A number of candidate stabilizers were incorporated in 5 mil thick samples of polypropylene film, and the resulting materials evaluated by heat aging the films. In some of the tests where indicated dilaurylthiodipropionate was added as synergist.

In the heat aging test, polypropylene film samples 5 mil in thickness were maintained in an oven at 140°C. Each sample was tested for loss of structural integrity. The number of hours shown in the table are the total elapsed hours before the film cracked or embrittled when flexed. The film was embrittled when it crumbled to a powder.

The resulting data are presented in Table IV.

TABLE IV

| Test No. | Compound | Percent by Weight Tetraphenolic Derivative | Percent by Weight Synergist | Oven Hours Cracked | Oven Hours Embrittled |
|---|---|---|---|---|---|
| 23 | Blank | 0 | 0 | 1 | 27 |
| 24 | α,α,α',α'-tetrakis(4-hydroxy-3,5-dimethylphenyl)p-xylene | 0.1 | 0 | 31 | 31 |
| 25 | α,α,α',α'-tetrakis(4-hydroxy-3,5-dimethylphenyl)p-xylene + dilaurylthiodipropionate | 0.1 | 0.3 | 602 | 644 |
| 26 | α,α,α',α'-tetrakis(4-hydroxy-3,6-dimethylphenyl)p-xylene | 0.1 | 0 | 30 | 30 |
| 27 | α,α,α',α'-tetrakis(4-hydroxy-3,6-dimethylphenyl)p-xylene + dilaurylthiodipropionate | 0.1 | 0.3 | 500 | 507 |

EXAMPLE 6

The solubility of some of the tetraphenolic derivatives prepared above in ethanol and toluene at 27°C. is reported in Table V.

TABLE V

| Test No. | Compound | Solubility (g/100 ml) Ethanol | Solubility (g/100 ml) Toluene |
|---|---|---|---|
| 28 | α,α,α',α'-tetrakis(4-hydroxy-3,5-dimethylphenyl)p-xylene | 3 | <.17 |
| 29 | α,α,α',α'-tetrakis(4-hydroxy-3,6-dimethylphenyl)p-xylene | <.14 | <.17 |
| 30 | α,α,α',α'-tetrakis(4-hydroxy-3-tert-butyl-5-methylphenyl)p-xylene | >9 | >9 |
| 31 | α,α,α',α'-tetrakis(4-hydroxy-3-tert-butyl-6-methylphenyl)p-xylene | >9 | <.17 |

The above Examples clearly demonstrate the accomplishment of this invention. Example 1 demonstrates our best mode for preparing the novel tetraphenolic derivatives of our invention.

Examples 2 and 3 further demonstrate the best mode of practicing our invention. Tests 1 –8 inclusive are embodiments of our invention. Tests 9–10 inclusive are not embodiments of our invention but were prepared for the purposes of comparison with our compositions in these and in the following examples. A comparison of the melting point given in Test 1 with Test 9 and a comparison of that in Test 3 with Test 10 shows that the tetra-2,6-disubstituted phenolic derivatives of our invention have lower melting points than the 2,5-derivatives.

In Example 4 a comparison of Tests 12 and 14 with Tests 13 and 15 respectively clearly demonstrates that our tetra-2,6-disubstituted phenolic derivatives are unexpectedly superior to the 2,5-derivatives as antioxidants in cis-polyisoprene. Tests 16–22 inclusive further indicate the effectiveness of our compositions as antioxidants in cis-polyisoprene.

In Example 5, a comparison of Test 24 with Test 26 and more particularly of Test 25 with Test 27 shows the unexpected superiority of our tetra-2,6-disubstituted phenolic derivatives over the prior art 2,5-derivatives. The superiority of our compositions as stabilizers for polypropylene is most evident when used in conjunction with a synergist.

Example 6 demonstrates by comparing Test 28 with Test 29 and Test 30 with 31 that our tetra-2,6-disubstituted phenolic derivatives have the same or greater solubility than the 2,5-derivatives in typical alcohol and hydrocarbon solvents. This facilitates easier distribution in organic material to be stabilized.

From the foregoing descriptions we consider it to be clear that the present invention contributes a substantial benefit to the antioxidant art by providing a new and useful antioxidant suitable for stabilizing organic materials normally tending to undergo oxidative deterioration.

We claim:
1. $\alpha, \alpha, \alpha', \alpha'$,-tetrakis (4-hydroxy-3,5-dibenzylphenyl) p-xylene.
2. $\alpha, \alpha, \alpha', \alpha'$-tetrakis [4-hydroxy-3,5-di(p-methylbenzyl)phenyl] p-xylene.

* * * * *